(12) United States Patent
Hartmann (10) Patent No.: US 11,156,594 B2
(45) Date of Patent: Oct. 26, 2021

(54) METHOD FOR SPECIFYING FRACTURE RESISTANCE OF MECHANICALLY STRESSED GLASS OR GLASS CERAMIC

(71) Applicant: Schott AG, Mainz (DE)

(72) Inventor: Peter Hartmann, Wiesbaden (DE)

(73) Assignee: SCHOTT AG, Mainz (DE)

( * ) Notice: Subject to any disclaimer, the term of this patent is extended or adjusted under 35 U.S.C. 154(b) by 0 days.

(21) Appl. No.: 13/904,442

(22) Filed: May 29, 2013

(65) Prior Publication Data

US 2013/0319048 A1 Dec. 5, 2013

(30) Foreign Application Priority Data

May 29, 2012 (DE) ...................... 10 2012 104 594.1

(51) Int. Cl.
| | |
|---|---|
| *C03B 20/00* | (2006.01) |
| *C03C 19/00* | (2006.01) |
| *G01N 33/38* | (2006.01) |
| *G01N 17/00* | (2006.01) |
| *G01N 3/20* | (2006.01) |
| *G06F 17/00* | (2019.01) |

(52) U.S. Cl.
CPC .......... *G01N 33/386* (2013.01); *C03B 20/00* (2013.01); *G01N 3/20* (2013.01); *G01N 17/00* (2013.01); *G06F 17/00* (2013.01); *C03C 19/00* (2013.01); *G01N 2203/0012* (2013.01); *G01N 2203/0067* (2013.01); *G01N 2203/0218* (2013.01); *G01N 2203/0688* (2013.01)

(58) Field of Classification Search
None
See application file for complete search history.

(56) References Cited

PUBLICATIONS

Haldimann, "Fracture Strength of Structural Glass Elements—Analytical and Numerical Modelling, Testing, and Design", Thesis No. 3671, Ecole Polytechnique Federale De Lausanne, (2006) pp. 1-222.*
Khorasani, "Design Principles For Glass Used Structurally", Report TABK-04/1025 Lund (2004).*
Duffy et al., "Reliability Analysis of Structural Ceramic Components Using a Three-parameter Weibull Distribution" (1992). Civil and Environmental Engineering Faculty Publications. 3, 12 pages. (Year: 1992).*
"Stress and Deflections in Beams", https://www.engineeringtoolbox.com/beam-stress-deflection-d_1312.html, Per Wayback Machine, Mar. 2012, 5 pages (Year: 2012).*
"Bayer Engineering Polymers—Part and Mold Design: Thermoplastics. A DesignGuide", Jan. 1, 2000, 174 pages (Year: 2001).*
SCHOTT technical Information No. 33, "Design strength of optical glass and Zerodur®", Schott AG Mainz, 10 pages, Oct. 2004. (Year: 2004).*

(Continued)

*Primary Examiner* — Lisa L Herring
(74) *Attorney, Agent, or Firm* — Ohlandt, Greeley, Ruggiero & Perle, L.L.P.

(57) ABSTRACT

A method for specifying the material of glass or glass ceramic components by either the minimum service life of a component as a function of a predefined mechanical stress or the mechanical resistance as a function of a predefined service life during which mechanical stress occurs. The method enables a leaner dimensioning of mechanically stressed glass and glass ceramic components.

4 Claims, 5 Drawing Sheets

(56) References Cited

PUBLICATIONS

Kerkhof, Frank, Richter, Herbert, and Stahn, Dieter. "Strength of Glass on the Dependence of Loading History." Freiburg i. Br. Fraunhofer Institute for Material Mechanics, 1981. 30 pp.
English Translation of Office Action dated Sep. 25, 2012 in corresponding German Application No. 10-2012-104-594.1, 4 pp.
Dutch Office Action dated Feb. 17, 2014 corresponding to Dutch Patent App. No. 138669, 16 pp.
Doyle, et al., "Design Strength of Optical Glass", Proceedings of SPIE, vol. 5176 Optomechanics, Oct. 2003, Bellingham, Washington, 2003, 12 pp.
Ritter, et al., "Effect of Test Environment on Stress-Corrosion Susceptibility of Glass", Journal of the American Ceramic Society, Blackwell Publishing Malden, MA, vol. 58, No. 7-8, Jul.-Aug. 1975, 3 pp.
Caprino, et al., "Fatigue of Glass Fabric/Epdxy Composites", Composites Part A: Applied Science and Manufacturing, Elsevier Science Publishers B.V., Amsterdam, NL, Mar. 1999, 6 pp.
Minimum lifetime of Zerodur structures based on breakage stress threshold model, Peter Hartmann, Optical Engineering 58(2), Feb. 2019.

\* cited by examiner

METHOD FOR SPECIFYING FRACTURE RESISTANCE OF MECHANICALLY STRESSED GLASS OR GLASS CERAMIC

CROSS REFERENCE TO RELATED APPLICATIONS

This application claims benefit under 35 U.S.C. § 119(a) of German Patent Application No. 10 2012 104 594.1, filed May 29, 2012, the entire contents of which are incorporated herein by reference.

BACKGROUND OF THE INVENTION

1. Field of the Invention

The invention generally relates to the characterization of material properties of products. More particularly, the invention relates to the determination of the resistance to fracture of mechanically stressed components, such as carrier structures.

2. Description of Related Art

There are so far no reliable methods known for determining the long-term stability of components made of materials whose stability is affected by the surface quality thereof. This criterion applies inter alia to brittle materials, such as glass and glass ceramics. Glass and glass ceramics are intrinsically very strong materials that break only under stresses where steel already failed. However, this strength is considerably influenced by the surface quality, in particular by the presence of cracks on the surface. Such cracks may reduce the mechanical stress limit by two orders of magnitude.

Furthermore, for some components a high reliability is required associated with a very low failure probability within a specified period of time which is different depending on the application. For the required low failure probabilities, in turn, few or no measured data are available. Therefore, for this range, in order to permit to specify the failure probability for a component made of a brittle material, or to permit to specify the allowable mechanical stress for a given failure probability, existing data are extrapolated. This results in very uncertain data in a range of low failure probabilities. Because of this uncertain data, material thicknesses of the components are rather oversized in order to avoid a failure of the component.

Therefore, an object of the invention is to improve the characterization of components in terms of their service life or permissible mechanical stress, and also to adapt the dimensioning of components accordingly in this way.

SUMMARY

Accordingly, the invention provides a method for specifying a glass or glass ceramic component by one of the following parameters: the minimum service life of a component as a function of a predefined mechanical stress; or the mechanical resistance as a function of a predefined service life, during which a mechanical stress occurs.

Specifying is based on the relationship $$t = \frac{\sigma_{B,r}^{n+1}}{\dot{\sigma}_r} \cdot \frac{1}{(n+1) \cdot \sigma_{B,c}^n} \quad (1)$$

wherein t is the minimum service life;
n is the stress corrosion coefficient of the material of the glass or glass ceramic component;
$\dot{\sigma}_r$ is a rate of stress increase;
$\sigma_{B,c}$ is the mechanical stress expressed as a mechanical tensile stress occurring during the service life of the component; and
$\sigma_{B,r}$ is the minimum strength of the component expressed as a mechanical tensile stress until fracture occurs under the effect of the mechanical stress in the component which increases according to the rate of stress increase $\dot{\sigma}_r$.

With the knowledge of these parameters, now a glass or glass ceramic component can be designed and manufactured accordingly so that it resists a predefined load without breaking for a specified period of time.

Accordingly, the method for producing a glass or glass ceramic component is based on the steps of: predefining a minimum service life of the component and a mechanical stress to which the component is exposed; determining the dimensions of the component such that under the predefined mechanical stress at least the predefined minimum service life is achieved without fracture of the component; forming the glass or glass ceramic component with the determined dimensions, wherein the determining of the dimensions of the glass or glass ceramic component is again based on the above relationship (1). The dimensions of the component are chosen such that the load to which the glass or glass ceramic component is exposed on average during the minimum service life does not cause tensile stresses in the material of the glass or glass ceramic component greater than $\sigma_{B,c}$ on average.

In this way, by assuming a predefined load it is ensured that the component does not fail at least within the minimum service life, or, vice versa, that at least the minimum service life is survived without fracture under a predefined stress.

Surprisingly, it has been found that by using the invention considerably slimmer dimensions are possible, for example smaller thicknesses of plate-shaped glass or glass ceramic elements, without affecting the intended purpose of application of the component or impairing the reliability thereof. This results in substantial weight savings, among other things.

The invention is furthermore based on the surprising finding that glass and glass ceramic components do not follow a standard Weibull distribution under increasing mechanical stress until fracture. Rather, surprisingly, there is a minimum strength, so that under mechanical loads up to this limit a failure can virtually be excluded.

Parameter $\sigma_{B,r}$ may be obtained by a series of measurements. According to one embodiment of the invention, the minimum strength $\sigma_{B,r}$ is determined by exposing a plurality of samples of the glass or glass ceramic material whose surface is preferably treated in the same or similar manner as the glass or glass ceramic component, to a mechanical tensile stress increasing by the rate of stress increase until each respective sample breaks. From the data of the load exerted upon fracture, the minimum strength $\sigma_{B,r}$ may then be determined as a threshold value.

The stress corrosion coefficient is material-specific and depends on the environmental conditions of the component. This coefficient may also be measured. Also, there are values found in the literature. Measuring methods for measuring the dimensionless stress corrosion coefficient are known for example from F. Kerkhof, H. Richter, D. Stahn, "Festigkeit von Glas, zur Abhängigkeit von Belastungsdauer und-Verlauf", Glastechn. Berichte 54 (1981), No. 8, pp. 265-277.

This document also gives an equation similar to relation (1) for the service life, however, in contrast to the invention this is in the form of a comparison of a plate afflicted by a crack of known depth with a crack-free plate. Instead, relation (1) rather uses a minimum strength which generally applies to specific glass or glass ceramic components having a defined surface for a specific rate of stress increase. This permits to more generally predict the lifetime and/or resistance to tensile stress for industrially manufactured glass or glass ceramic components, even without deep cracks.

The dimensions of the component do not have to be chosen in a manner so that for a required minimum service life the required mechanical strength is just achieved. Rather, it is generally advantageous when the component is dimensioned larger, especially as significantly higher mechanical stabilities will result anyway when compared to the dimensioning previously employed for glass or glass ceramic components. Thus, according to one embodiment of the invention, the component may be sized in a manner so that the predefined minimum service life is extended by up to 50%, or so that a mechanical resistance of the component without fracture of up to 50% greater than $\sigma_{B,c}$ is achieved.

Relationship (1) is furthermore based on the finding that even without visible deep cracks in near-surface zones of the glass ceramics, defects may be present, such as in particular micro-cracks, which are then decisive for the service life of the component when subjected to tensile stresses. These cracks will grow under the influence of tensile forces at the surface. Crack growth is also influenced by the environment. For example, in a humid environment a crack is growing faster than in vacuum or in a dry atmosphere. This material and environmental property is accounted for with stress corrosion coefficient n (also known as stress corrosion cracking coefficient). Coefficients n are known for a multitude of glasses and glass ceramics.

Some examples of stress cracking coefficients are listed below:

a) For Zerodur glass ceramics, n may be assumed as a very conservative value from 27 to 33 in air at a relative humidity between 30% and 60%. From the literature, measured values between 50 and 55 are known. Values of n in a range from 50 to 55 also apply to vacuum and under inert conditions.

b) The following values have been assumed for soda-lime glass in the literature:
   n=16 for a crack under water;
   n=18.1 for a crack in a glass surface in air at a relative humidity of 50%; and
   n=70 under inert conditions or in vacuum.

According to a modification of the invention, the stress corrosion coefficient may be measured in a simple manner. In particular, for this purpose a plurality of samples may be exposed to an increasing mechanical load until fracture, using different rates of stress increase. The stress corrosion coefficient may then be determined using the following relationship:

$$\ln(\sigma_f) = \frac{\ln(\dot{\sigma})}{n+1} const. \tag{2}$$

wherein $\sigma_f$ is the tensile stress at fracture of the sample and $\dot{\sigma}$ is the rate of stress increase. Relation (2) may then be fitted to the measured values by varying the parameter const. and the stress corrosion coefficient n, and in this way the stress corrosion coefficient n may be determined. Fitting may be accomplished by a best fit, for example. In a double logarithmic representation of fracture tensile stress as a function of the rate of stress increase, the stress corrosion coefficient is the slope of a straight line.

DESCRIPTION OF THE DRAWINGS

The invention will now be described by way of exemplary embodiments and with reference to the accompanying drawings. In the drawings, the same reference numerals designate the same or equivalent elements.

DETAILED DESCRIPTION

Figure 1:
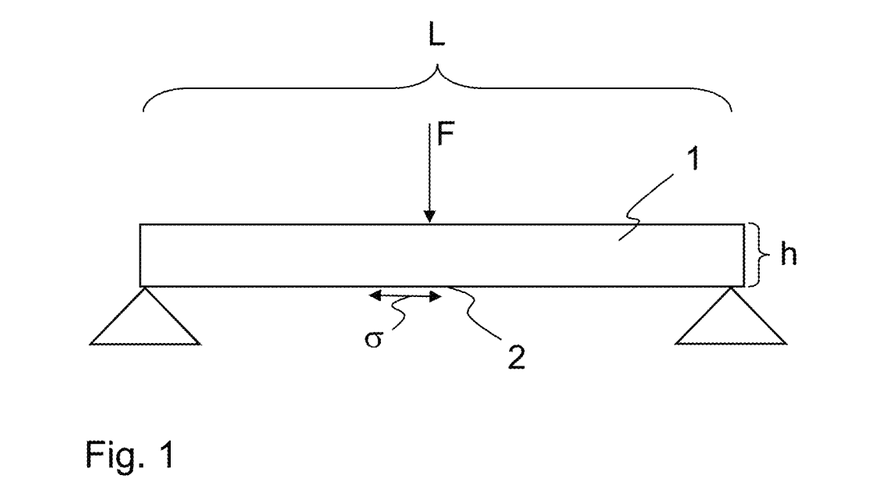
FIG. 1 schematically illustrates a mechanically loaded glass or glass ceramic component.

Referring to FIG. 1, one exemplary embodiment will be explained of how a value for the required mechanical strength may be determined when dimensioning the component, expressed as the maximum tensile stress occurring in the glass or glass ceramic material based on the mechanical stress occurring during use of the component.

The glass or glass ceramic component 1 in this exemplary embodiment is a carrier which is supported at both ends thereof. In this embodiment, the carrier is exposed to a force F at the center thereof. This causes a tensile stress σ at a surface 2 of the carrier, due to this mechanical load and associated deflection. In the ideal case, the resulting compressive stress at the other surface has the same magnitude. Since the tensile stress is more critical for the strength of glass or glass ceramic components, only this tensile stress will be considered below.

The following applies to the maximum tensile stress $\sigma_{max}$ occurring at the central extreme fiber of the carrier:

$$\sigma_{max} = \frac{F \cdot L}{4 \cdot W_y}, \tag{3}$$

wherein F is the applied force in newtons, L is the length of the carrier in meters, and $W_y$ denotes the section modulus in cubic meters. The following applies to the section modulus:

$$W_y = \frac{I_y}{h/2}, \tag{4}$$

wherein h denotes the height of the carrier, and $I_y$ denotes the axial planar moment of inertia in meters. In case of a rectangular carrier, the following applies to $I_y$:

$$I_y = \frac{A \cdot h^2}{12}, \tag{5}$$

wherein A denotes the cross-sectional area in square meters of the carrier and h denotes the height in meters. Thus, in this simple case, the maximum tensile stress for the carrier to which a force F is applied, for example by being loaded by a weight resting thereupon results as:

$$\sigma_{max} = \frac{3F \cdot L}{2A \cdot h}. \quad (6)$$

Calculation methods for more complex geometries are known to those skilled in the art. For example, a finite element calculation may be used for components 1 of more complex shapes.

The component may now be dimensioned and produced accordingly, so that during the required minimum service life and predefined mechanical stress the maximum tensile stress does not reach or exceed the minimum strength $\sigma_{B,r}$ that can be determined from relationship (1) given above. In this way, the component is dimensioned such that the predefined minimum service life is at least achieved under the predefined mechanical stress, i.e. under the force F in the example of FIG. 1.

Figure 2:
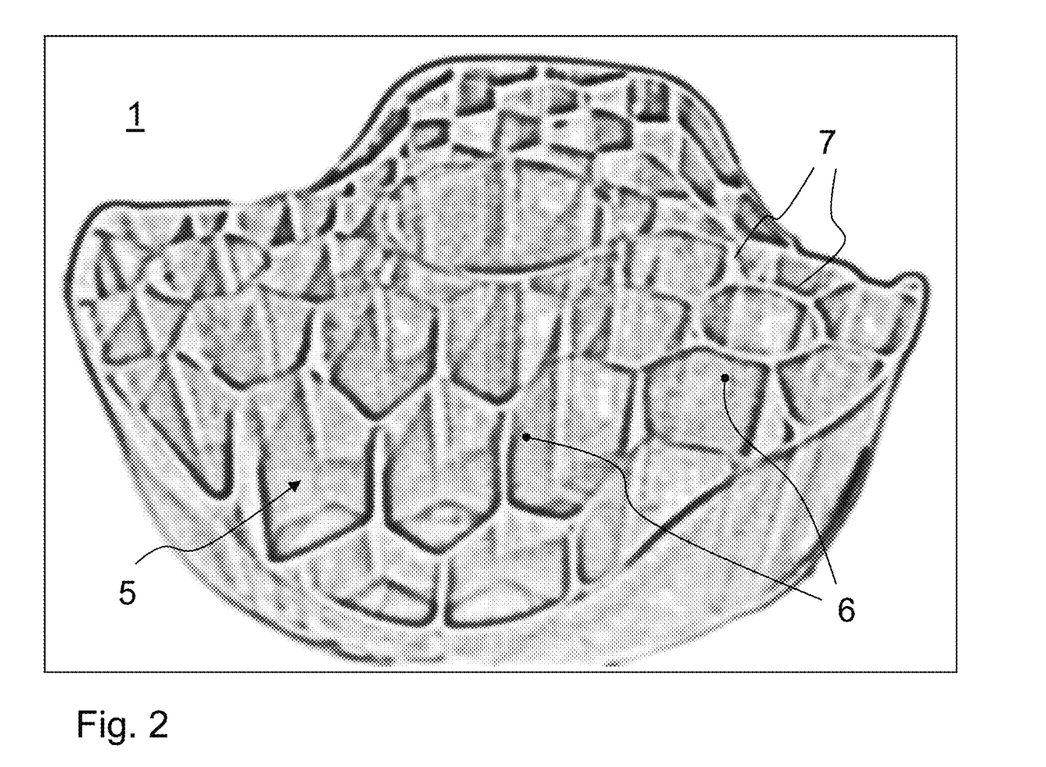
FIG. 2 shows an embodiment of a glass ceramic component.

FIG. 2 shows one embodiment of a glass or glass ceramic component 1 in form of a lightweight carrier. The carrier is made of Zerodur glass ceramics and has a honeycomb structure in order to provide a particularly high mechanical strength combined with a low weight. Such glass ceramic components are used in the aerospace industry, for example. The glass ceramic component is composed of webs 6 that form honeycombs 5. In this case, when component 1 is subjected to a load, the highest tensile stresses will typically occur at the edges 7 of webs 6.

Such components experience high mechanical loads especially when starting the launch vehicle, but these loads are mainly generated by the acceleration of the launch vehicle and therefore only occur for a few minutes. Therefore, in this case, the component may be dimensioned such that although it has to resist to a high mechanical load, this is only for a short period, for example from 5 to 15 minutes. The component is preferably designed so that the minimum service life is longer than the duration of the occurring mechanical stress. In other words, the dimensions of component 1 are determined in a way so that under the predefined mechanical stress the predefined minimum service life is at least achieved without fracture and is preferably exceeded, so that component 1 will be still intact even after the minimum service life and under the mechanical stress. In the illustrated example, the dimensioning may be accomplished by setting the width of webs 6, for example. When the width of the webs is increased, the tensile stress at the edges 7 of webs 6 decreases for the same mechanical load.

With reference to the following drawings, this determining of the dimensions which is accomplished using relationship (1), and the specifying of the strength and durability of glass and glass ceramic components 1 according to the present invention will be explained in further detail.

Figure 3:
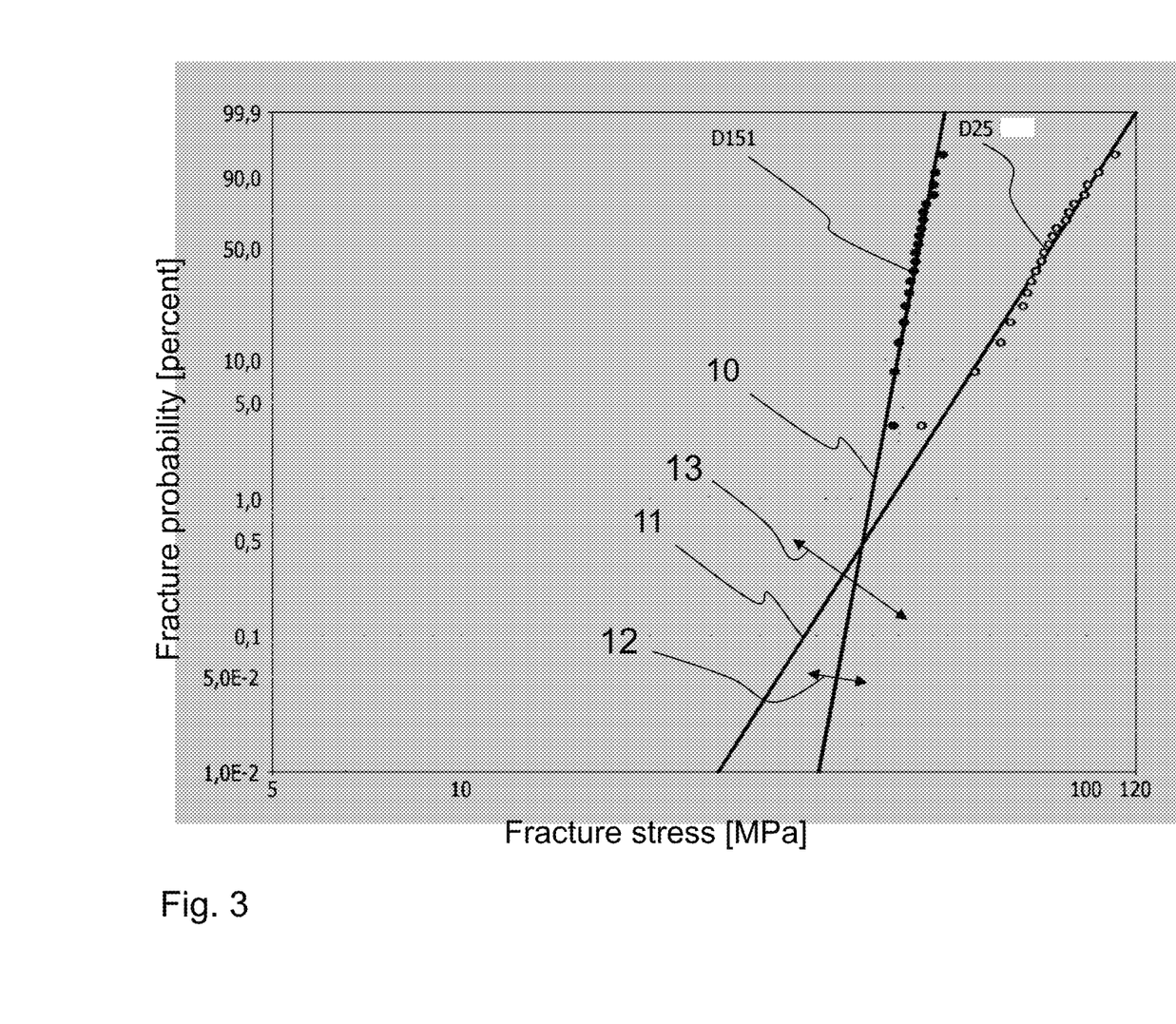
FIG. 3 is a graph of measured fracture strengths of glass ceramic samples.

Referring to FIG. 3, the problem of the prior art in dimensioning glass or glass ceramic components is first illustrated. FIG. 3 shows a diagram in the form of a Weibull network into which the readings of two series of breaking strengths of Zerodur glass ceramic samples have been plotted.

The two series differ in the surface treatment of the samples. The measured values marked "D151" were measured on samples whose surface had been polished with an abrasive of a maximum grain size of 151 μm. The measured values marked "D25" were measured on samples that had been polished using a mean grain size of 20 μm. It can be seen from the different breaking strengths that the surface treatment of glass or glass ceramic components has an effect on the breaking strength. It is the glass ceramic treated with a finer grain size, i.e. the smoother one, that exhibits a higher fracture strength.

Two-parameter Weibull distributions were fitted to the respective measured values. Here, curve 10 represents the Weibull distribution for measurement series "D151", and curve 11 represents the Weibull distribution for measurement series "D25". The Weibull distribution is given by:

$$F(\sigma) = 1 - e^{-\left(\frac{\sigma}{\sigma_c}\right)^\lambda}; \quad (7)$$

wherein σ is the tensile stress. Commonly, in a Weibull distribution, $\sigma_c$ is referred to as a location parameter, and λ is referred to as a shape parameter. Additionally indicated are the 95% confidence intervals 12, 13 of distributions 10, 11. Surprisingly, curves 10 and 11 intersect at lower failure probabilities. This would mean that in a range of low fracture probabilities which is important for a high reliability, the intrinsically stronger glass ceramic with a smoother surface is less resistant than the rougher glass ceramic. If one follows the fitted Weibull distribution 11 and wants to ensure that the respective glass ceramic component does not fail in any way, this would mean that only very low tensile stresses can be permitted and that the component has to be dimensioned with an appropriate width.

When additionally considering the confidence interval, it will be apparent from FIG. 3 that for low failure probabilities of 0.01% a tensile stress of 10 MPa should not be exceeded in the component. Obviously, the problem with this approach is the necessary extrapolation of data over several orders of magnitude of the fracture probability. In addition, a fracture cannot be completely excluded here, since the two-parameter Weibull distribution begins at the origin not shown in FIG. 1.

The invention is inter alia based on the finding that the two-parameter Weibull distribution is not suitable to correctly reflect the range of low fracture probabilities.

Figure 4:
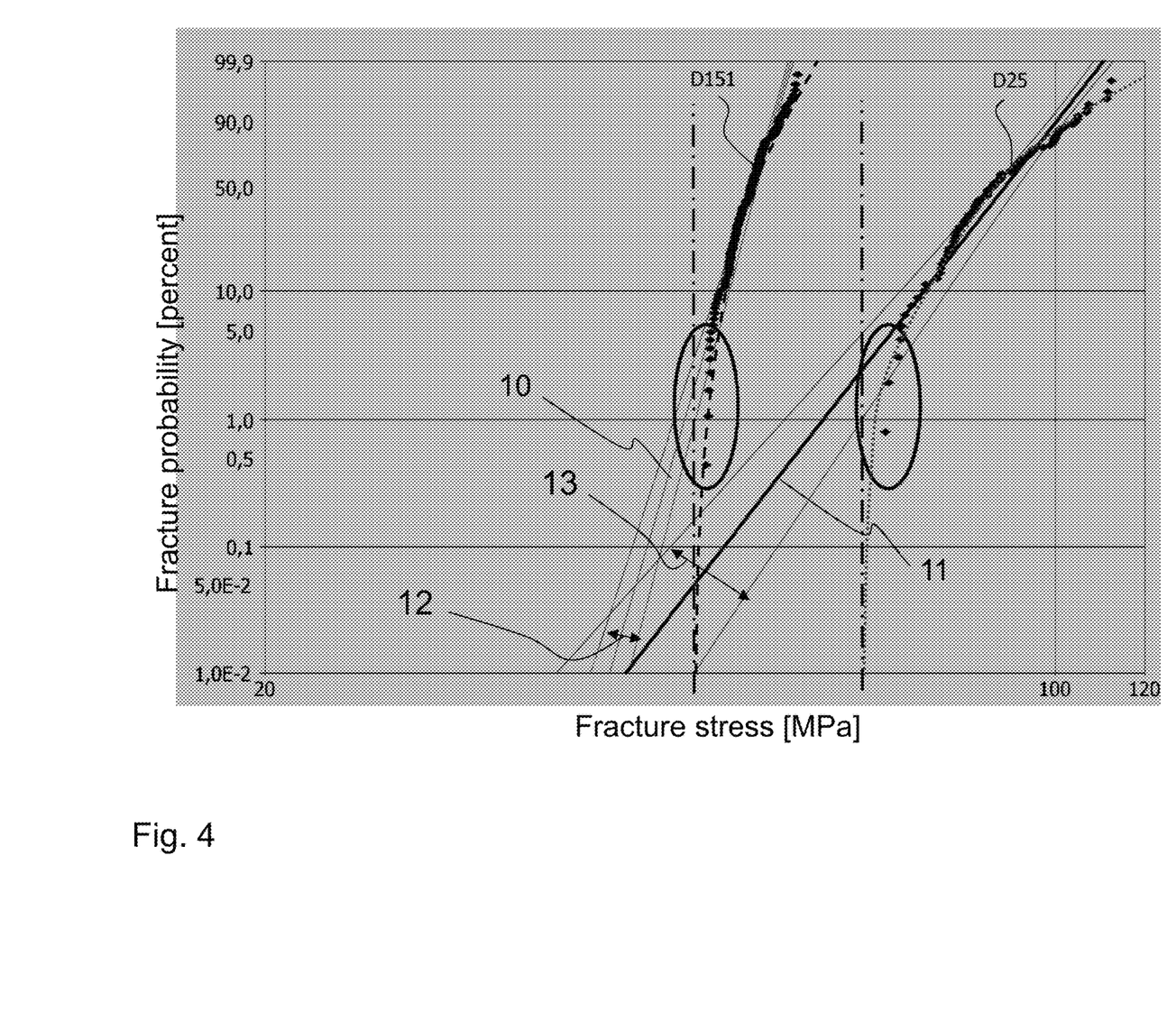
FIG. 4 is a graph of measured fracture strengths with an extended data set.

This is apparent from an expanded set of data which is shown in the diagram of FIG. 4. Data sets "D151" and "D25" again represent the fracture strengths determined from the samples polished using the respective grain sizes. There are now data available also for lower fracture stresses which are correspondingly rare due to the low fracture probability. These ranges of the two measurement sets are encircled and highlighted by ovals. Apparently herein there is a clear systematic deviation from a fit using a two-parameter Weibull distribution. In particular, it is apparent from FIG. 4 that the two sets of measurement data tend to a threshold value of fracture stress. Below that threshold value of minimum strength $\sigma_{B,r}$ no fracture may occur, at least not within the time determined from the rate of stress increase $\dot{\sigma}_r$ used in the measurement. This applies at least as far as the sample has no further damage. In the example shown in FIG. 4 the rate of stress increase $\dot{\sigma}_r$ was 2 MPa per second. To the measured values of both measurement series, a three-parameter Weibull distribution may be fitted very well, which is given by:

$$F(\sigma) = 1 - e^{-\left(\frac{\sigma-\gamma}{\eta}\right)^\beta}. \quad (8)$$

This function is determined by the three parameters γ, η, and β, and may be fitted to the measured values by varying these parameters. In particular, the three-parameter Weibull distribution disappears in case the tensile stress σ assumes the value of γ. Therefore, this parameter may be assumed as the minimum strength $\sigma_{B,r}$ when fitting a three-parameter Weibull distribution to the measured values. For tensile stresses lower than or equal to this value, the fracture probability is zero.

Therefore, according to one embodiment of the invention without limitation to glass ceramics or Zerodur as a specific material it is suggested that the minimum strength $\sigma_{B,r}$ is determined by subjecting a plurality of samples of the glass or glass ceramic material to a mechanical tensile stress increasing according to the rate of stress increase $\dot{\sigma}_r$ until the respective sample breaks, and then the minimum strength $\sigma_{B,r}$ is determined as a threshold value from the data of the load exerted at fracture, by fitting a three-parameter Weibull distribution to the measured values, and the minimum strength is determined as that tensile stress at which the Weibull distribution is equal to zero. For safety reasons, a slightly smaller minimum strength may be used in this case, preferably a tensile stress lower by not more than 20% than the tensile stress at which the Weibull distribution disappears. However, it is also possible to provide any other safety factor in the dimensioning of the components.

In the example shown in FIG. 4, a minimum strength of 47.3 MPa is now obtained as the limit of the Weibull distribution for measurement series "D151", and a minimum strength of 67.7 MPa for measurement series "D25". Thus, when compared with the usual previous dimensioning of Zerudur components for tensile stresses of not more than 10 MPa, the invention permits to dimension components considerably different, in particular considerably lighter, without any increase in failure probability under the intended load. This applies as long as the surface of the component subjected to tensile stress has the same, comparable or similar properties. The reason for the different tensile strengths depending on the surface treatment are microcracks in the surface. Although these are usually not even visible, they nevertheless affect the strength. This is in particular because cracks in glass and glass ceramics, even the smallest, will grow under a tensile stress on the surface.

For crack growth, the following differential equation can be applied:

$$\frac{da}{dt} = A \cdot (\sigma \sqrt{a} \cdot f)^n \quad (9)$$

In this relationship, a is the crack length, A is a material constant, σ is the tensile stress, f is the crack shape factor which may be set to f=2 in general, and n is again the stress corrosion coefficient. Relation (1) in principle results therefrom by solving the differential equation (9) with a constant tensile stress σ and constant rate of stress increase $\dot{\sigma}_r$.

By measuring the stress cracking coefficient it is now possible to characterize the material of glass or glass ceramic components 1 in terms of the minimum service life as a function of a predefined mechanical stress, or of the mechanical strength as a function of a predefined service life during which a mechanical stress occurs. The following FIGS. 5 and 6 show such characterizations for the example of Zerodur glass ceramics.

Figure 5:
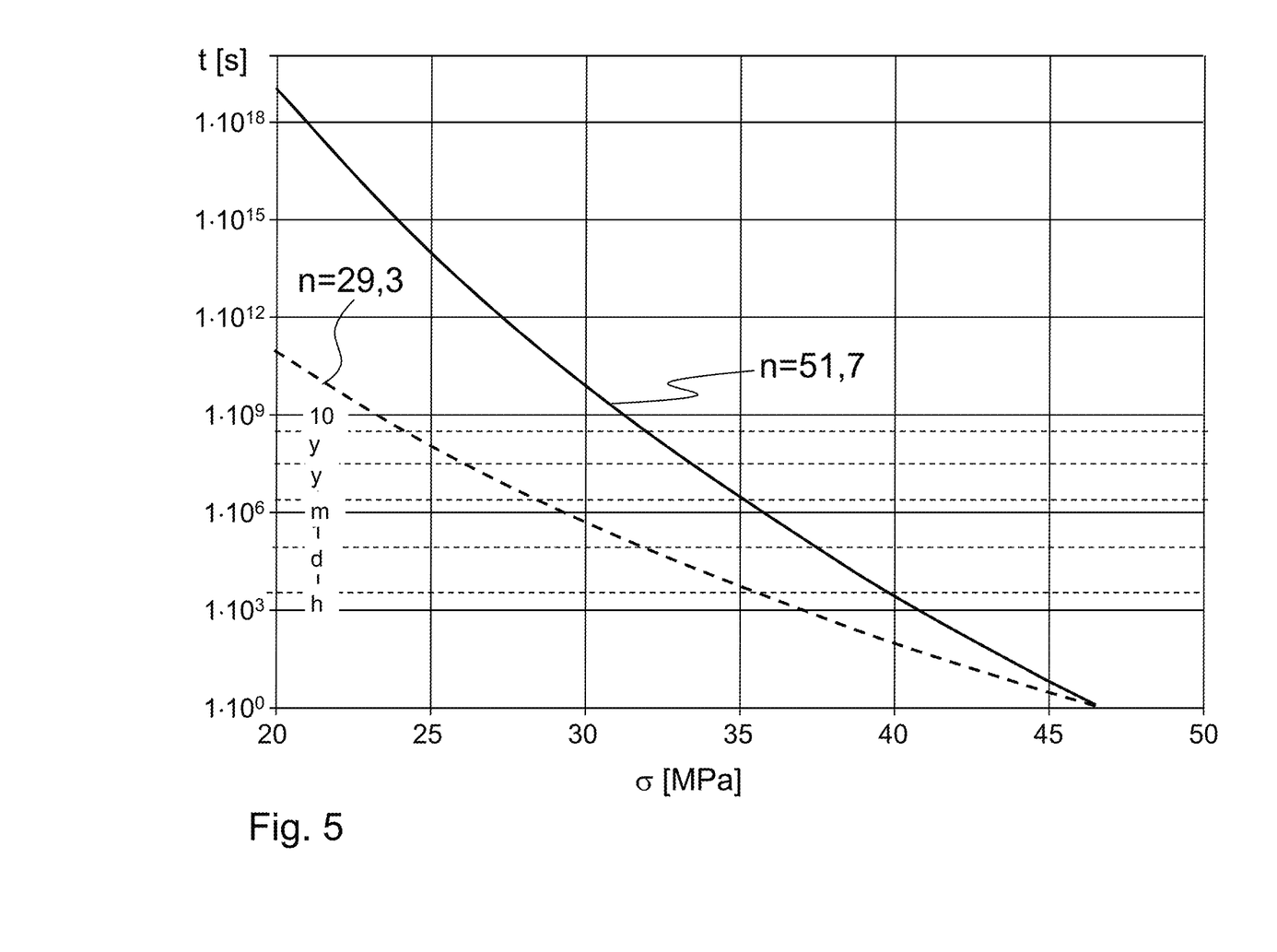
FIGS. 5 and 6 are graphs of the service life as a function of the mechanical stress.
Figure 6:
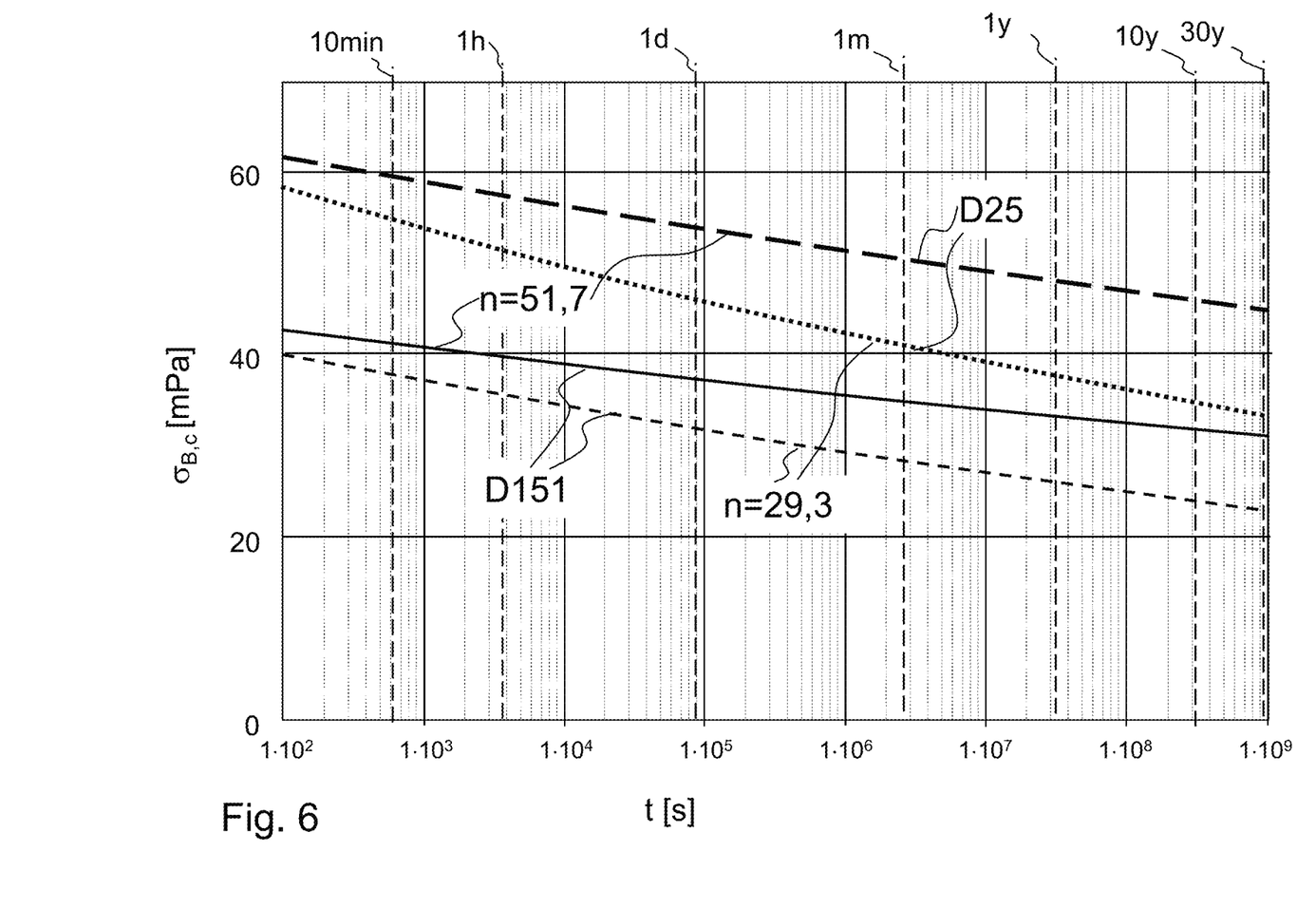

FIG. 5 shows the minimum service life t plotted logarithmically as a function of the tensile stress σ occurring in the component. The curves resulting from relation (1) are plotted for two stress corrosion coefficients n=29.3 and n=51.7 as measured on Zerodur glass ceramics. Here, the value of n=29.3 was measured on glass ceramics for crack corrosion in moist air. In another measurement, the value of n=51.7 was determined for crack corrosion at normal room humidity, but may also be assumed as a value for crack corrosion in vacuum. Both curves were determined for a glass ceramic polished using a grain size of not more than 151 µm. That is, these curves apply to glass ceramic components that have been surface treated according to data set "D151" shown in FIG. 4.

Additionally, lines for specific service lives are indicated in the diagram, namely line 1 h for a minimum service life of one hour, line 1 d for a minimum service life of one day, line 1 m for a minimum service life of one month, and lines 1 y and 10 y for minimum service lives of one and 10 years, respectively. The line at $1*10^9$ seconds approximately corresponds to a service life of 30 years.

If, for example, the glass ceramic component is intended for use as a component of a satellite, such as a mirror or a carrier for a mirror, high mechanical loads will only occur temporarily during the launch of the carrier rocket. So if a minimum service life of one hour is demanded here under the mechanical stress occurring during the launch of the rocket, which already includes a security window, the component can now be dimensioned to have a strength of 35 MPa. This is based on the assumption that during launch of the rocket the component will still be in air of normal humidity, so that the curve of stress corrosion coefficient n=29.3 applies. By contrast, if the component is in the rocket in an inert atmosphere, the curve of n=51 may be applied. In this case, the component may be dimensioned to exhibit a mechanical strength of about 40 MPa. Therefore, when compared with the tensile stresses of 10 MPa as previously applied, a component can be dimensioned significantly thinner based on the invention without any increase in fracture probability. Considering for example the component shown in FIG. 2, this means that the width of edges 7 may be reduced by a factor of three or even slightly more. Therefore, a corresponding component will weigh only a fraction of a component dimensioned according to previous guidelines, without any need to accept a higher probability of fracture.

FIG. 6, in turn, shows a diagram of the mechanical strength expressed as the mechanical stress $\sigma_{B,c}$ to be expected during the use of the component as a function of the minimum service life t plotted logarithmically. Additionally illustrated are the lines "10 min" and "30 y" for minimum service lives of 10 minutes and 30 years, respectively. The data are again based on the minimum strengths determined using measurement series "D151". Accordingly, the two curves of stress corrosion coefficients n=29.3 and n=51.7 are designated "D151".

As is already apparent from FIG. 4, the mechanical strength and the minimum service life resulting under mechanical stress can be significantly increased if the surface is treated to be smoother. For this purpose, FIG. 6 additionally illustrates two curves for the mechanical strength of a Zerodur glass ceramic component whose surface has been treated according to the samples of measurement series "D25". The two curves again differ in the underlying stress corrosion coefficients of n=29.3 and n=51.7. As is apparent from a comparison of the curves for the same stress corrosion coefficient, the mechanical resistance increases by more than 40% due to a polishing with a finer grain size. Even more evident is the increase in minimum service life. For example, the minimum service life of the component polished using a grain size of 151 μm is 100 seconds under a mechanical load of 40 MPa. In contrast, the minimum service life of the component polished using a maximum grain size of 25 μm is about $3*10^6$ seconds, i.e. increases by more than four orders of magnitude.

Generally it can be seen herefrom that an abrasive surface treatment increases the strength and durability of glass and glass ceramic components, without limitation to the exemplary embodiments. Therefore, according to one embodiment of the invention it is generally suggested that at least the surface of the glass or glass ceramic component that is subjected to tensile stress is treated by an abrasive technique after being formed. The reason for the enhancement in strength is that this abrasive treatment removes surface areas that exhibit micro-cracks.

A particularly high increase in strength and durability may be obtained according to still another embodiment of the invention by removing material from the surface of the glass ceramic component subjected to a tensile stress by etching. Especially effective in this case is a combination of abrasive removal and subsequent etching. The following values were measured on Zerodur glass ceramics: As already mentioned above, a minimum strength of 47.3 MPa resulted from measurements series "D151". If a surface polished in this manner is additionally etched so that in addition 83 μm of material is removed from the surface, the value of the minimum strength increases to 79.9 MPa.

The invention is particularly suitable for manufacturing glass or glass ceramic components in the aerospace field, such as for satellite-based telescope mirrors or mirror supports, as well as for carriers in microlithography steppers. In this case, both carriers for the masks as well as for the wafers to be exposed are considered. Important for these carriers, on the one hand, is a very low thermal expansion, on the other the masks and wafers are moved at very high accelerations, with correspondingly high mechanical loads.

It will be apparent to those skilled in the art that the invention is not limited to the embodiment illustrated by way of the figures but may be varied in many ways. For example, the invention has been described with reference to measurements on Zerodur glass ceramic parts. Of course it is likewise possible according to the invention to dimension and manufacture other components from other glass ceramics.

What is claimed is:

1. A method for producing a glass or glass ceramic component, comprising:
    exposing a plurality of samples of glass or glass ceramic material whose surface is treated in the same manner as the glass or glass ceramic component so that the plurality of samples have the same surface quality as the glass or glass ceramic component to a mechanical tensile stress that is increasing by a rate ($\dot{\sigma}_r$) in MPa/s until each of the plurality of samples fractures to obtain a mechanical tensile stress upon fracture ($\sigma_f$) in MPa for each of the plurality of samples;
    fitting a three-parameter Weibull distribution to the mechanical tensile stress upon fracture ($\sigma_f$) in MPa for the plurality of samples and setting a minimum strength ($\sigma_{B,r}$) in MPa as that tensile stress threshold at which the Weibull distribution becomes zero or which is lower by not more than 20% than the tensile stress threshold;
    predefining a minimum service life (t) in seconds intended from the glass or glass ceramic component;
    calculating a mechanical tensile stress ($\sigma_{B,c}$) from the relationship:

$$t = \frac{\sigma_{B,r}^{n+1}}{\dot{\sigma}_r} \cdot \frac{1}{(n+1) \cdot \sigma_{B,c}^n},$$

with n being a stress corrosion coefficient of a material of the glass or glass ceramic component;
    setting a maximum stress ($\sigma_{max}$) in MPa to which the glass or glass ceramic component is designed to be exposed to less than or equal to the mechanical tensile stress ($\sigma_{B,c}$);
    calculating a section modulus ($W_y$) in cubic meters of the glass or glass ceramic component from the maximum stress ($\sigma_{max}$) using a predefined applied force (F) in Newton across a predefined length (L) in meters to which the glass or glass ceramic component is designed to be exposed from the relationship:

$$\sigma_{max} = \frac{F \cdot L}{4 \cdot W_y};$$

and
    forming the glass or glass ceramic component with the section modulus ($W_y$).

2. The method of claim 1, further comprising calculating the stress corrosion coefficient using the relationship:

$$\ln(\sigma_f) = \frac{\ln(\dot{\sigma})}{n+1} + const.$$

that is fitted to measured values of the plurality of samples by varying a parameter constant (const.), wherein $\sigma_f$ is a tensile stress at fracture of a sample of the plurality of samples.

3. The method of claim 1, further comprising using the section modulus ($W_y$) in cubic meters and an axial planar moment of inertia ($I_y$) in meters to the fourth of the glass or glass ceramic component to calculate a height (h) in meters of the glass or glass ceramic component from the relationship:

$$W_y = \frac{I_Y}{h/2}.$$

4. The method of claim 3, wherein, when the glass or glass ceramic component has a rectangular cross section, the axial planar moment of inertia ($I_y$) is calculated from the relationship:

$$I_y = \frac{A \cdot h^2}{12},$$

wherein A denotes a cross-sectional area in square meters of the glass or glass ceramic component.

* * * * *